(12) United States Patent
Tang

(10) Patent No.: US 10,258,497 B2
(45) Date of Patent: Apr. 16, 2019

(54) FEMALE CONDOM WITH ADHERING SHIELD AND METHOD OF MANUFACTURE

(71) Applicant: John Ing Ching Tang, Sarawak Sibu (MY)

(72) Inventor: John Ing Ching Tang, Sarawak Sibu (MY)

(*) Notice: Subject to any disclaimer, the term of this patent is extended or adjusted under 35 U.S.C. 154(b) by 461 days.

(21) Appl. No.: 14/781,276

(22) PCT Filed: Jan. 10, 2014

(86) PCT No.: PCT/IB2014/058166
§ 371 (c)(1),
(2) Date: Sep. 29, 2015

(87) PCT Pub. No.: WO2014/177946
PCT Pub. Date: Nov. 6, 2014

(65) Prior Publication Data
US 2016/0051399 A1    Feb. 25, 2016

(30) Foreign Application Priority Data

Apr. 30, 2013  (MY) ............................. PI2013001552

(51) Int. Cl.
*A61F 6/06* (2006.01)
*A61F 6/04* (2006.01)
(Continued)

(52) U.S. Cl.
CPC ................ *A61F 6/065* (2013.01); *A61F 6/04* (2013.01); *B29C 65/48* (2013.01);
(Continued)

(58) Field of Classification Search
CPC ...... A61F 6/04; A61F 6/065; A61F 2006/041; A61F 2006/047; A61F 2006/048;
(Continued)

(56) References Cited

U.S. PATENT DOCUMENTS 4,856,534 A * 8/1989 Sorkin ...................... A61F 6/04
                                                          128/844
5,351,698 A * 10/1994 Wheeler ................... A61F 6/04
                                                          128/844

(Continued)

*Primary Examiner* — Keri J Nelson
(74) *Attorney, Agent, or Firm* — Maschoff Brennan

(57) ABSTRACT

The present invention is a female condom with an extended shield that can cover and seal the external genitalia to prevent sperm and disease transmissions during coitus. The construction of the present invention involves sealing of the double layered membranous films in an omega or similar shape to create a tubular and a shield portions, followed by applications of adhesive and releasing sheets onto the exterior of both shields before it is cut into the final product. The tubular portion will form the protective barrier for vagina (condom) while the shield portion, which adheres to the external genitalia, will prevent the seepage of body fluid. The tubular portion may be inverted to serve as a male condom. Double tubular portions are constructed for unconventional sexual activities. Transverse and longitudinal folds are created to enlarge the tubular portion. The female condom may be shaped, textured, colored and flavored according to the users' demand.

19 Claims, 10 Drawing Sheets

(51) Int. Cl.
    *B29C 65/48*     (2006.01)
    *B29C 65/00*     (2006.01)
    *A61B 46/27*     (2016.01)
    *A61B 46/13*     (2016.01)
    *A61B 46/17*     (2016.01)
    *A61B 46/00*     (2016.01)
    *B29L 31/00*     (2006.01)

(52) U.S. Cl.
    CPC .......... *B29C 66/0326* (2013.01); *A61B 46/13* (2016.02); *A61B 46/17* (2016.02); *A61B 46/27* (2016.02); *A61B 46/30* (2016.02); *A61F 2006/041* (2013.01); *A61F 2006/047* (2013.01); *A61F 2006/048* (2013.01); *A61F 2006/049* (2013.01); *B29L 2031/7538* (2013.01)

(58) Field of Classification Search
    CPC ... A61F 2006/049; A61B 46/13; A61B 46/17; A61B 46/27; A61B 46/30
    USPC ...................... 128/830, 842, 844, 918; 602/3
    See application file for complete search history.

(56) References Cited

U.S. PATENT DOCUMENTS

| | | | |
|---|---|---|---|
| 5,490,525 A * | 2/1996 | Reddy | A61F 6/04 128/842 |
| 5,622,185 A * | 4/1997 | Richardson | A61F 6/065 128/842 |
| 5,758,659 A * | 6/1998 | Thompson | A61F 6/04 128/844 |
| 2005/0115568 A1* | 6/2005 | Martin | A61F 6/065 128/844 |
| 2006/0042639 A1* | 3/2006 | Wallace | A61F 6/065 128/830 |
| 2013/0160774 A1* | 6/2013 | Schuman | A61F 6/04 128/844 |

* cited by examiner

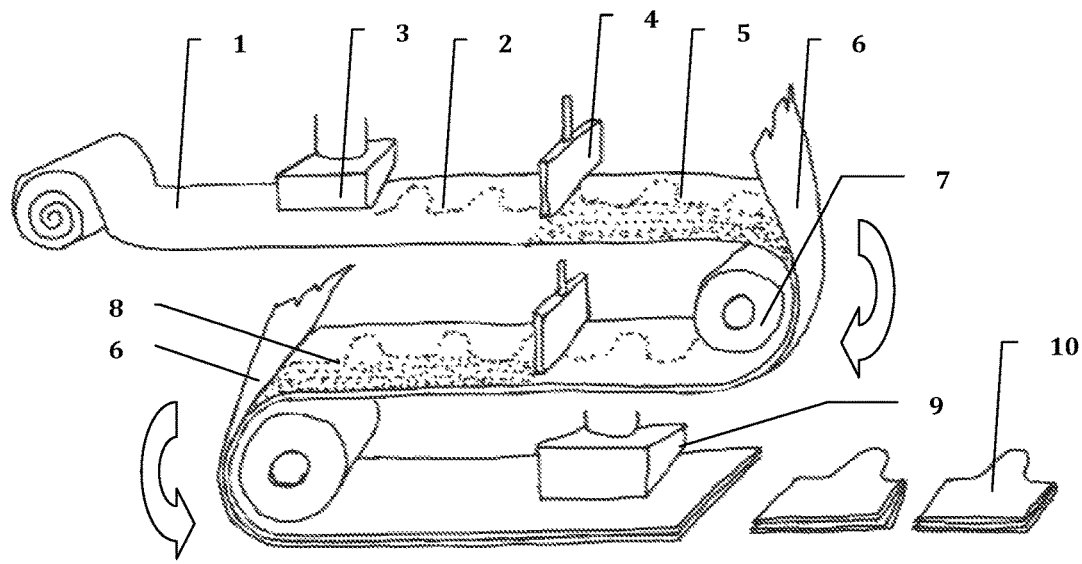
Fig. 2
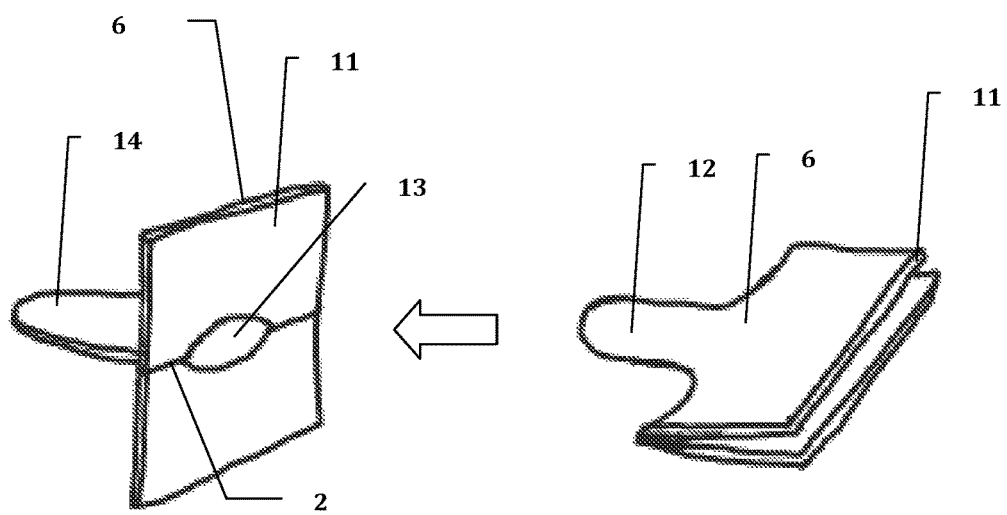
Fig. 3b                    Fig. 3a

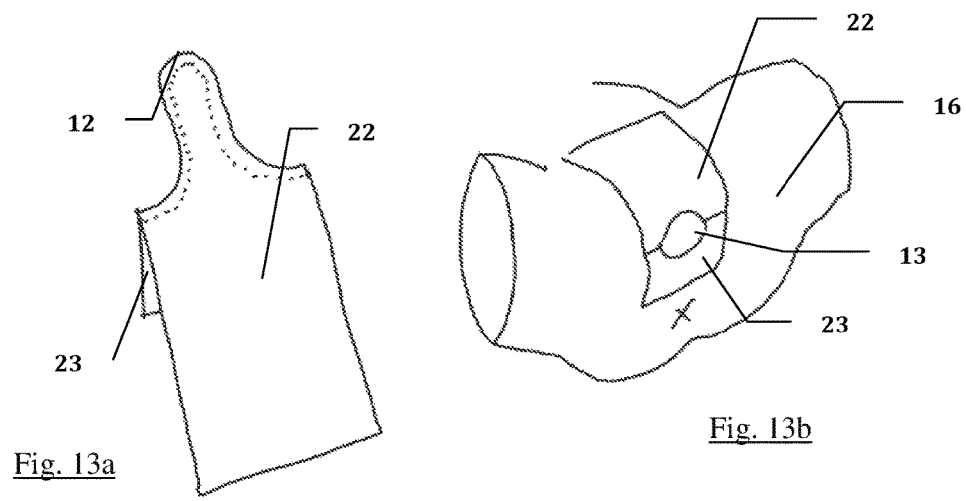
Fig. 13a
Fig. 13b
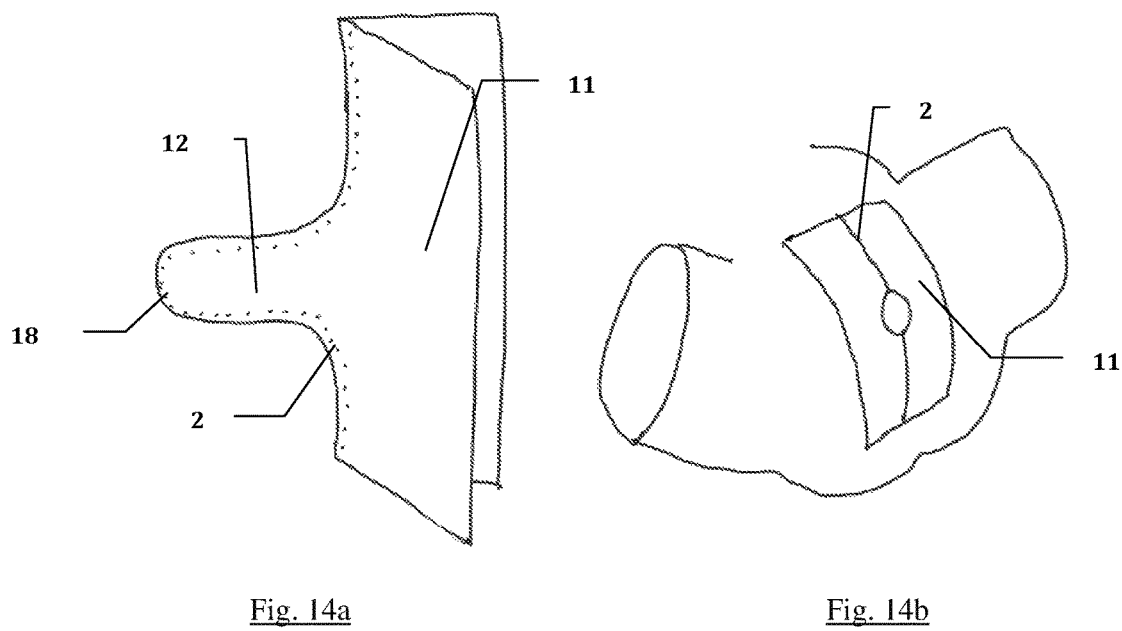
Fig. 14a
Fig. 14b

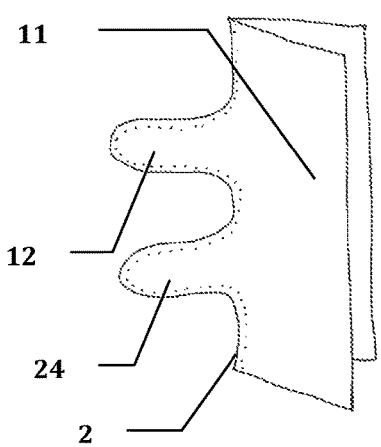
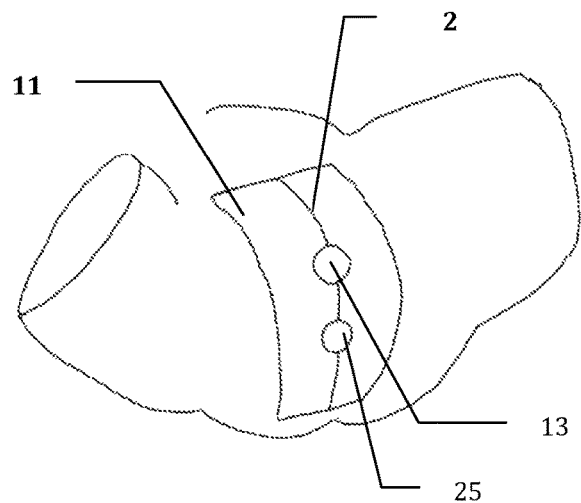
Fig. 15a  Fig. 15b
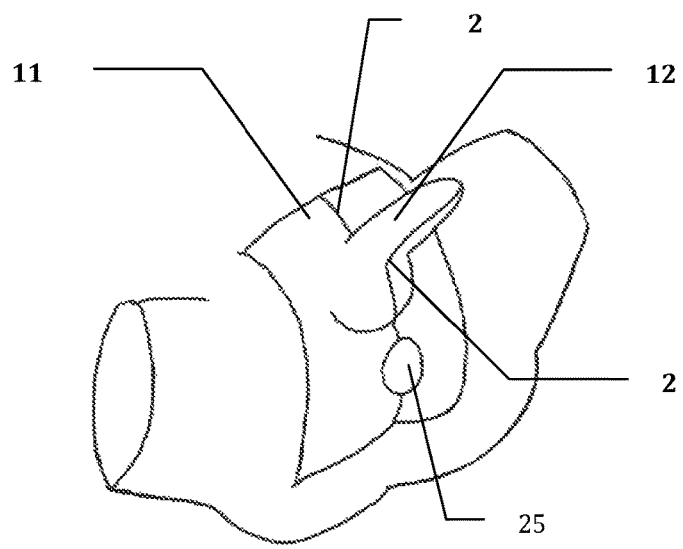
Fig. 15c

FEMALE CONDOM WITH ADHERING SHIELD AND METHOD OF MANUFACTURE

CROSS-REFERENCE TO RELATED APPLICATIONS

This application is a National Phase Application under 35 USC 371 of PCT/IB2014/058166, filed Jan. 10, 2014 (published as WO/2014/177946), which claims priority to Malaysian Application No. PI2013001552, filed on Apr. 30, 2013. The disclosure of the prior application is considered part of and is incorporated by reference in its entirety in the disclosure of this application.

TECHNICAL FIELD

The objective of the present invention is related to sexual barriers for prevention of fertilizing spermatozoa and sexually transmitted diseases (STD) during sexual intercourse. Particularly it relates to the protection of both the internal and external genitalia of either sexual partner to prevent exchange of body fluid by a thin flexible walled female condom with an extended shield. It is yet another object of the present invention to provide a device that is cheaper to produce and easier to use than the prior art.

BACKGROUND ART

The need to create a good barrier contraceptive and anti-infective device has never been greater. The world population is constantly on the rise, so are the unplanned and unwanted pregnancies. STD, especially AIDS, are widespread in many parts of the world. Many attempts at the barrier methods have been made to counter this trend, some to certain success, but none has been able to be truly effective in both contraception and disease prevention.

The problems with the familiar condom are well known. It depends on the rigidity of the unreliable penis to stay in place. Furthermore it only covers the body of the penis and not the base, therefore unable to prevent diseases, such as herpes and warts, through the external genital, anal or oral contact. In addition, it depends on the male partner's willingness to use it. It is also not user friendly. Unrolling it in dim lighting often ends up in the wrong direction, and its strangulating pressure decreases the tactile sensation of the penis.

Female condoms thus provide viable alternatives to male condoms.

U.S. Pat. No. 5,094,250 (FIG. 1a) to Hessel describes a thin wall tubular device with a closed end and an open end. It has an inner ring at the closed end positioned at the cervix and an outer ring at the open end positioned at the introitus. The device only partially shields the external genitalia and it does not seal up the introitus. Therefore it does not prevent infections through direct contact of external genitalia or the exchange of body fluid. Furthermore, it is more expensive to produce than a regular condom.

To address the above issues of preventing exchange of body fluid and shielding the external genitalia to achieve better contraception and disease prevention during coitus, U.S. Pat. No. 5,269,320 (FIG. 1b) to Hunnicutt describes a rubber female condom with an extended shield at the open end. The shield covers the external genitalia, pudendum, and is secured in place by an adhesive. The shield may be formed as part of a panty or men's brief. The tubular portion is provided in a compacted, folded state, and together with the shield portion, it is covered by releasing paper on both sides.

U.S. Pat. No. 4,898,184 (FIG. 1c) to Skurkovich et al describes a similar female condom made of rubber latex, but with greater shield area held in place by weak adhesive or straps around the genitalia.

U.S. Pat. No. 5,515,862 (FIG. 1d) to Artsi describes yet another similar female condom with an even larger shield that is sealingly attached to or integrally formed with the open end, said shield having six well defined regions which together form a continuous, seamless surface surrounding the open end, the surface having a continuous outer edge. An adhesive is applied close to, and around the entirety of the outer edge beyond the pubic hairline to resist seepage of fluid during coitus. The tubular portion is provided in the folded manner like a concertina, as seen in the invention of Hunnicutt.

All the three aforementioned female condoms with the adhering shield are made of a thin soft water-impermeable material, for instance rubber latex or other biologically acceptable plastic films, such as polyurethane, polyethylene, polypropylene, polyester, nylon, polyvinyl chloride, bioplastics, nitrile and others. As the shield portion has a plane which is perpendicular or at an angle to the tubular portion, the constructions of these female condoms are complicated, let alone the difficulty in the application of adhesive onto the flimsy shield, as the tubular portion is situated at the centre of the shield. If rubber latex is used as described in the construction in the aforementioned prior art of FIG. 1b and 1c, a complex molding process and adhesive application will be needed, so the cost of production will be high. On the other hand, if a thin flexible membranous film is used, one would not be able to create a "continuous, seamless surface" for the shield as described by Artsi, and membranous film will be difficult to handle due to its flimsiness. For example, to fold the thin membranous tubular portion into a concertina as described by Artsi would be technically difficult.

There is therefore a need for female condoms with adhering shield that can be manufactured at a low cost and can be easy to handle, while providing a secured barrier for both internal and external genitalia to effectively prevent unplanned pregnancies and transmission of STD during coitus.

SUMMARY OF THE INVENTION

In accordance with the present invention there is provided a prophylactic device that is to be worn by a person to prevent the transmission of STD and sperm during sexual intercourse. The device is a female condom which comprises two layers of flexible, thin membranous films, such as such as rubber, polyurethane, polyethylene, polypropylene, polyester, nylon, polyvinyl chloride, bioplastics, nitrile, silicone and others, sealed together in an omega or similar shape. The sealing can be performed by using heat, chemical, mechanical, light, electrical or other source of energy. The seam that forms the base of the omega shape has two elongated flanges which at separation from one another, form the shield portion of the female condom, while the tubular space thus created by the omega shape becomes the female condom consisting of a closed end and an open end. The diameter of the said open end is constructed to be sufficiently large to permit insertion and movement of a penis, while the length of the said tubular space is sufficiently long enough to accommodate the entire penis. The said shield portion is constructed to be sufficiently large to seal the entire external genitalia to prevent seepage of fluid from female genitalia. It can be enlarged to cover more area of the lower part of the body to prevent direct dermal contacts between the external genitalia of the user and her partner.

In all the different embodiments mentioned herewith, the said omega shape's tubular portion can be replaced by other similar shapes, such as a narrow bell shape or a rectangular shape or a combination of these.

Another feature of the present invention is the application of adhesive to the external surface of the shield portion together with releasing paper or plastic sheet. Another feature of the present invention is that the adhesive can be applied partially or wholly on both the tubular and shield portions. Anything that keeps the membranous shield portion in place can be used as "adhesive". It can range from static electricity to industrial glue such as poly-isobutylenes, polysiloxanes and polyacrylate; weak adhesive such as hydrogel, or non-adhesives such as petroleum jelly, lanolin, ointment, cream, lotion, grease, honey and syrup etc. The advantage of the later would be the ability of adjustment of the shield portion after deploying the female condom and painless removal of the shield from the hairy skin. It also allows easy removal of the flimsy female condom without breaking it, thus avoiding the possible spillage of seminal content in the vagina.

Another feature of the present invention is the adhesive could be medicated with spermicides and/or other antiseptics. It may also be enriched with health supplements such as vitamins or minerals.

Another feature of the present invention is the pre-treatment of the internal and/or external lining of the said tubular portion to be textured with ridges, studs, nubs and so on to enhance the sexual stimulation, to reduce the electrostatic field or to reduce the luminal size of the vagina, especially in multi-parous women.

In another embodiment of the present invention the said shield (and tubular portion) can be designed to be in various shapes, sizes, colours, opacity, textures, added pictures, wordings and logos to improve protection, aesthetic look and sexual appeal.

Another feature of the present invention is that the sizes and shape of the tubular and shield portion can be made according to: (1) different body build of the users, and (2) the preferred area of coverage for the external genitalia and the lower part of the body.

Another feature of the present invention is the size and shape of the anterior and posterior part of the shield can be the same or different to suit individual preferences.

In another embodiment of the present invention the female condom can be lubricated, perfumed and/ or flavoured to make it "look good, smell good, taste good and feel good".

In another embodiment, the tubular portion of the present invention can be inverted to turn it into a male condom.

In another embodiment, the omega shape seeling of the thin membranous films is performed longitudinally, resulting in the two parts of the shield being opened up side way instead of being anterior-posteriorly.

Another embodiment is having two, instead of one, omega shape sealing of the thin membranous films longitudinally to create two tubular portions enabling both vaginal and anal intercourses for both female and male users.

In yet another embodiment, the tubular portion is folded longitudinally into one or multiple folds before sealing. The resulting tubular portion will then have a greater circumference for a given width, thereby giving less strain to the open end of the female condom.

In yet another embodiment, both layers of thin membranous films are transversely folded into double layers (for example, 5 to 25 mm) at the closed end of the tubular portion before sealing. The resulting closed end of the tubular portion will then have a wider diameter than the open end at opening up, therefore allowing a more secured placement of the ring pessary at the closed end, which is used to anchor the female condom in the vagina.

In yet another embodiment of the present invention, the female condom is made up of sealing of more than two pieces of thin membranous films each making up a part of both the tubular and shield portions. In yet another embodiment, the releasing paper/plastic sheet is textured to allow it to be easily identified by touching.

BRIEF DESCRIPTION OF THE DRAWINGS

The invention is herein described, by way of example only, with reference to the accompanying drawings, wherein:

FIG. 2: Brief schematic plan of the manufacturing process of the current invention;
FIG. 3a: Female condom in perspective view right before deployment;
FIG. 3b: Perspective view of the female condom with the shield portion opened up ready for deployment;
FIG. 11b: Perspective view of the female user after deployment of the device in FIG. 11a;
FIG. 13a: Perspective view of the female condom with an unequal length of the shield portions anterior and posteriorly.
FIG. 13b: Perspective view of the female condom after deployment of the condom in FIG. 13a on a female user.
FIG. 14a: Perspective view of the female condom where the omega shaped sealing runs longitudinally;

FIG. 14b: Perspective view of the female user after deployment of the female condom as in FIG. 14a;

FIG. 15a: Perspective view of the female condom with double omega shaped healing sealing running longitudinally;

FIG. 15b: Perspective view of the female condom in FIG. 15a after deployment on a female user;

FIG. 15c: Perspective view of the female condom in FIG. 15a, where one tubular portion has been inverted to become male condom, at deployment on a male user;

DESCRIPTION OF THE PREFERRED EMBODIMENTS

Figure 1A:
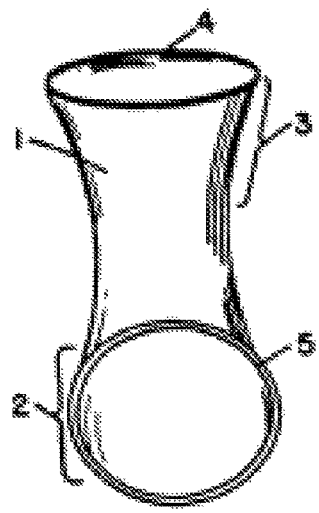
FIG. 1a: Female condom according to Hessel.
Figure 1B:
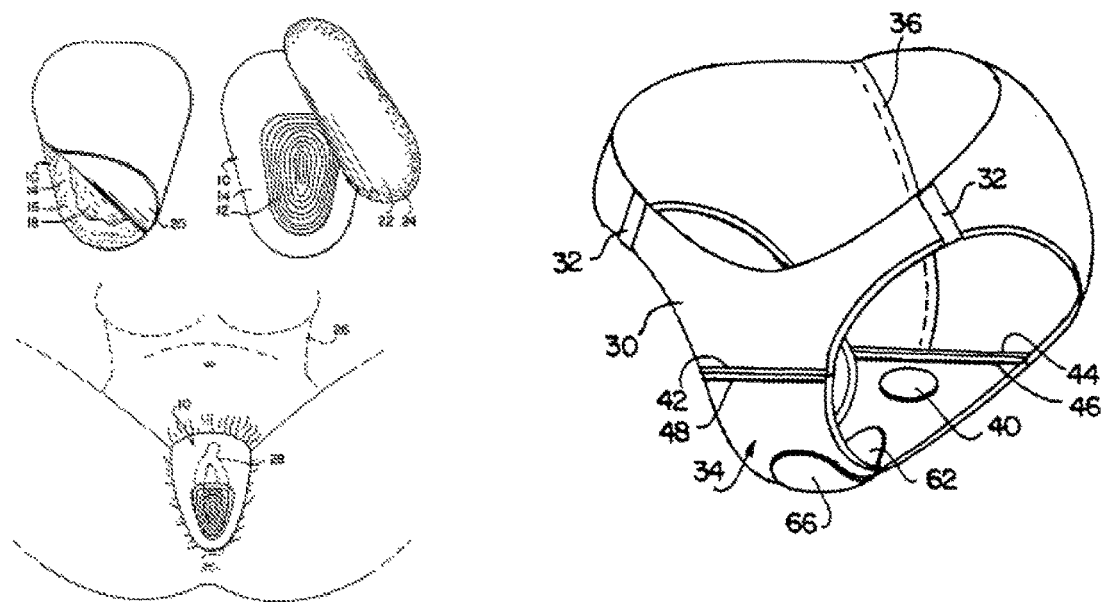
FIG. 1b: Female condom according to Hunnicutt.
Figure 1C:
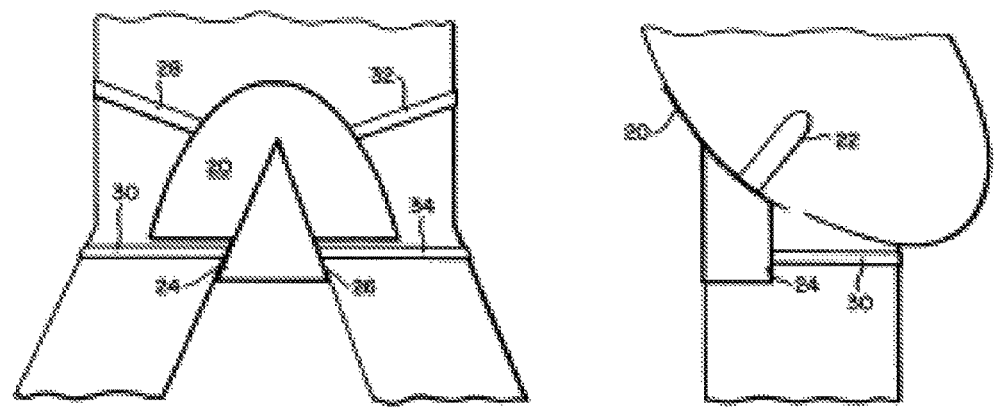
FIG. 1c: Female condom according to Skurkovich.
Figure 1D:
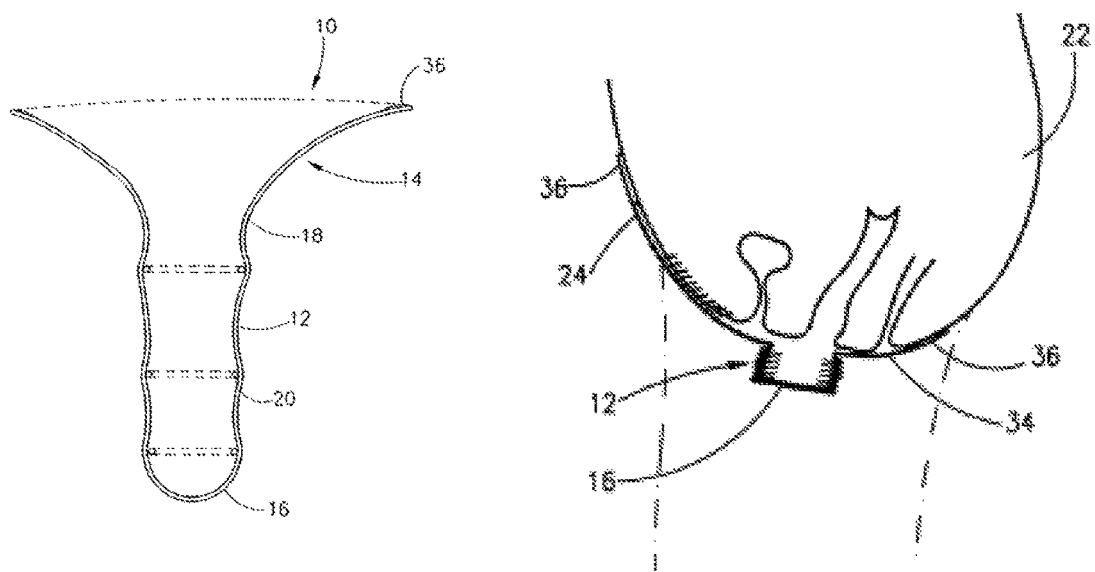
FIG. 1d: Female condom according to Artsi.

The present invention is of female condom with an extended adhering shield portion to protect the external genitalia and to prevent the transmission of the sperms and STD during sexual intercourse.

The principle and the operation of the present invention could be understood with reference to the above drawings with the following description.

A brief schematic plan of the construction of the preferred embodiment of the present invention is laid down in FIG. 2. It explains how the preferred embodiment could be produced at an efficient and low cost manner, and at the same time shading light on how it is deployed. The double layer thin flexible thermoplastic films 1 would roll out onto the manufacturing table, much like the production of the supermarket plastic bags. Here it is heat sealed into omega or similar shape in quick successive stamping 3. One of the "adhesive" mentioned above 4 is partially or wholly applied to the portion of the membranous films 5 below the seam at the base of the omega shapes 2. Non absorbing releasing paper or plastic sheet 6 is then applied onto the entire width of the membranous films The product is rolled over 7 to have the adhesive and the releasing sheet applied on the external surface of the opposing membranous film in the same manner 8. An alternative method is to approaching the opposing surface from opposite direction simultaneously, thus allowing simultaneous application of adhesive and releasing paper for both surfaces. Yet another method is to apply the adhesive onto the releasing paper before attaching it to the membranous film. Now that the double layer sealed membranous films with the adhesive applied is completely covered with releasing sheet on both sides, it is cut 9 into the final product 10 by using techniques such as stamp or roller cutting.

The cutting edges for the tubular portion are set to be near the seam, while the said lower portions that would make up the shield portion 11 would be cut in a straight or a curve line perpendicular or at an angle to the seam at the base of omega shape 2.

The membranous films may be pre-treated before sealing as aforementioned, such as being painted with pictures or wordings, or textured. Thus the shape of the shield 11 could be constructed to vary according to the type of pre-treatment. In order to ease the deployment of the condom, supporting/backing sheet can be attached to the inside of the shield portion prior to sealing. Likewise, the releasing paper/plastic sheet can be textured to facilitate its removal by touch.

Other manufacturing processes may be made within the scope and the spirit of the present invention. Examples of such variation may include the 'adhesive' being applied partially or wholly to either or both the tubular and the shield portion of the female condom, the application of the adhesive and the releasing sheet after the membranous films are cut, or using other methods of sealing, such as laser welding or dielectric bonding etc, on the membranous films.

Figure 4A:
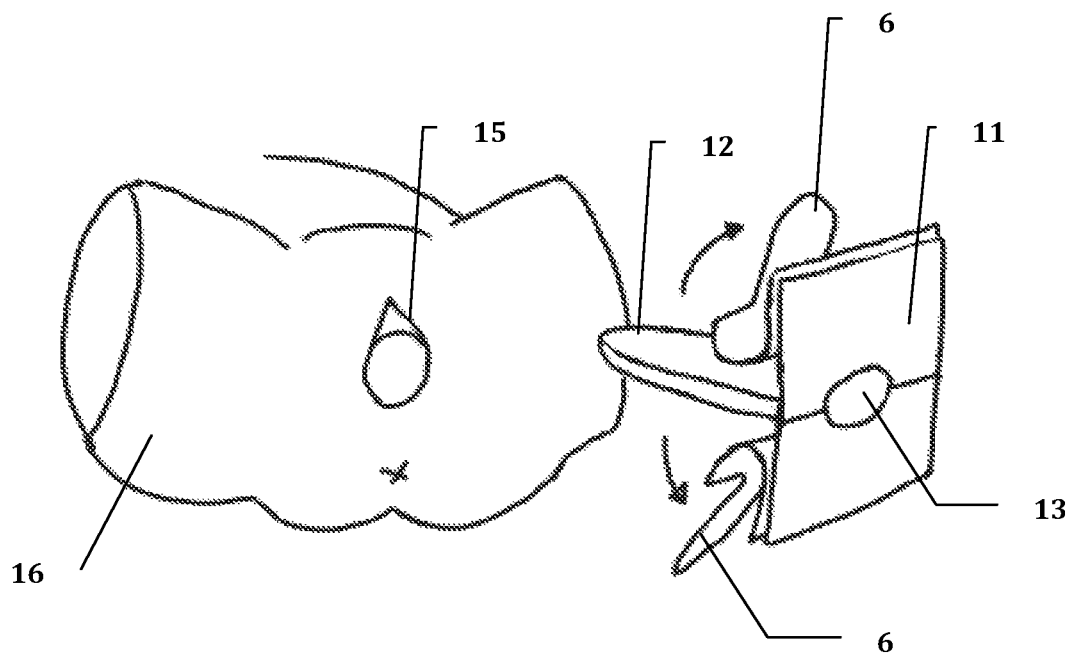
FIG. 4a: Perspective view of the female condom when the releasing sheets are partially peeled off.
Figure 4B:
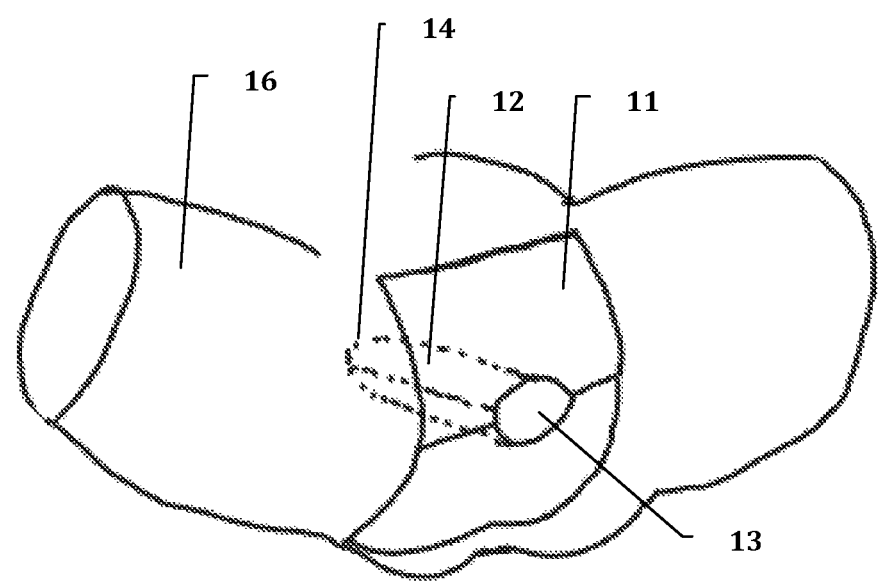
FIG. 4b: Perspective view of the female condom properly deployed onto the genitalia of the female user.
Figure 5A:
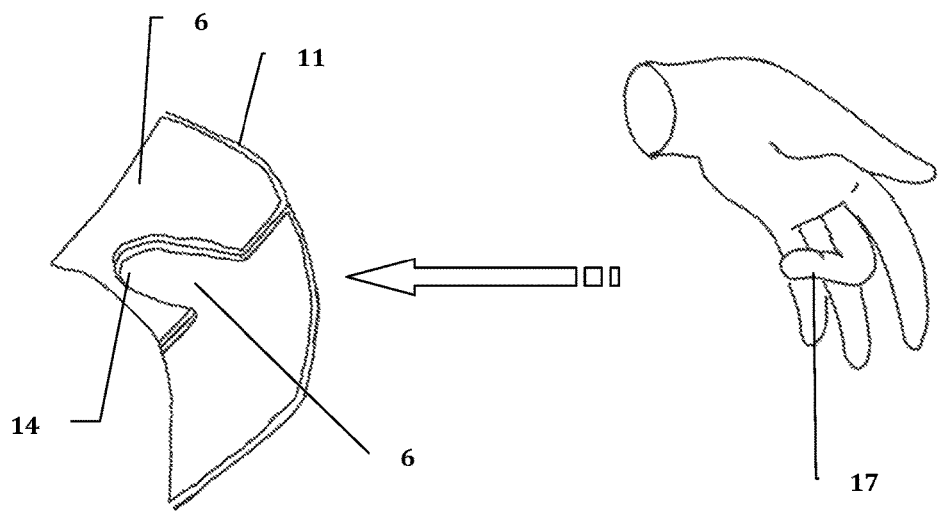
FIG. 5a: Perspective view of the insertion of middle finger into the tubular portion of the female condom.
Figure 5B:
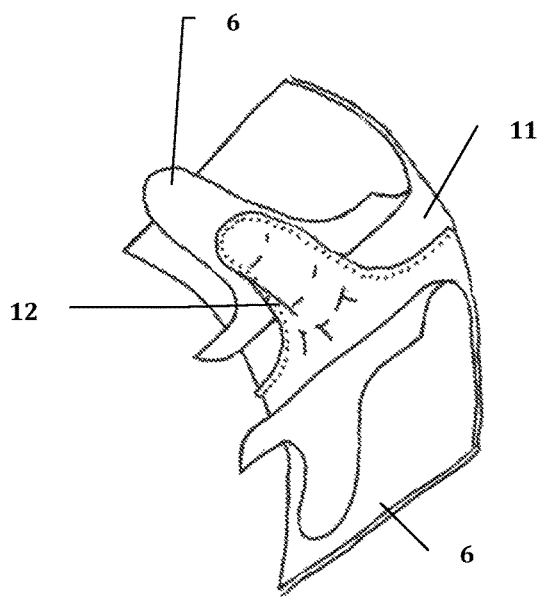
FIG. 5b: Perspective front views of FIG. 5a as the releasing sheets are being removed.
Figure 5C:
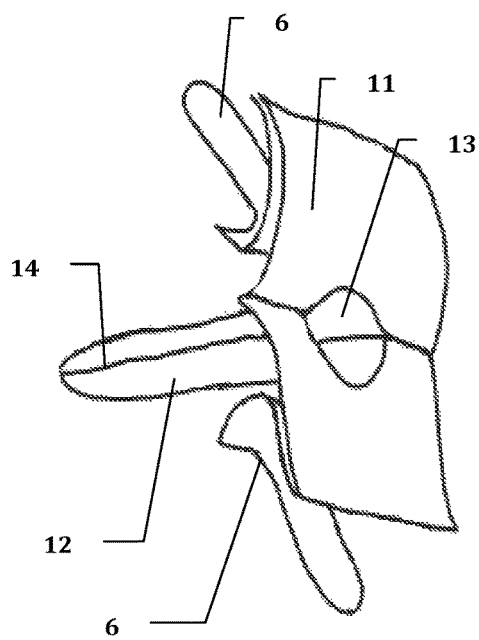
FIG. 5c: Perspective back view of FIG. 5b.

In anticipation of sexual activity, the female partner 16 would open up the two parts of the shield 11 that hinges at the sealed seam at the base of the omega shape 2 as shown in FIGS. 3a and 3b. She would then insert a lubricated middle finger 17 or an introducer/applicator into the said tubular open end 13 all the way up to the said closed end 14 (FIG. 5a). With that the exterior of the tubular portion is lubricated and inserted into the vagina 15 (FIG. 4a). While the said covered middle finger 17 is still inside the vagina, the palm and four other extended fingers of the same hand would press the shield portion 11 against the skin of external genitalia, and the anterior releasing paper or sheet 6 would be peeled off slowly with the other hand (FIG. 5b). The posterior releasing paper or sheet 6 would then be peeled off in the same manner. To facilitate easy recognition by touch, the releasing paper may be textured. Once the said shield 11 is securely adhered to the external genitalia (FIG. 4b), the said middle finger is removed from the tubular portion, which is to remain inside the vagina. Though not essential, a semi rigid ring 27 (FIG. 16b and c) or any anchoring device may be inserted and placed at the said closed end 14 of the tubular portion to further secure the tubular portion in the vagina. The backing/supporting sheets, if present, are then duly peeled off from the shield portion.

After the sexual activity, the shield 11 would be peeled off from the external genitalia followed by removal of the tubular portion 12 from the vagina and discarded.

Figure 6A:
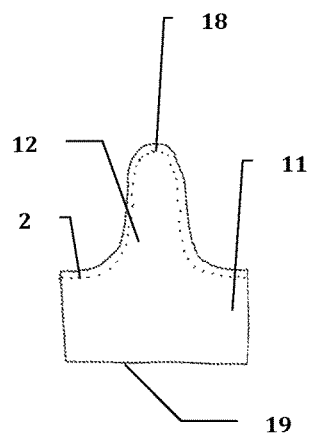
FIG. 6a: Front view of the female condom.
Figure 6B:
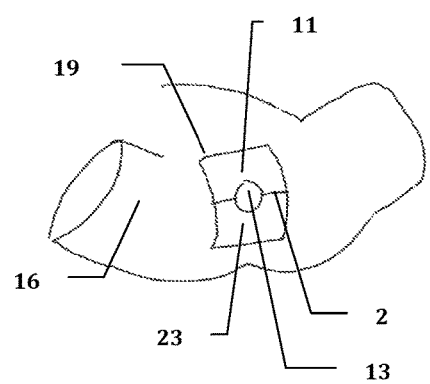
FIG. 6b: Perspective view of female condom after being deployed.
Figure 6C:
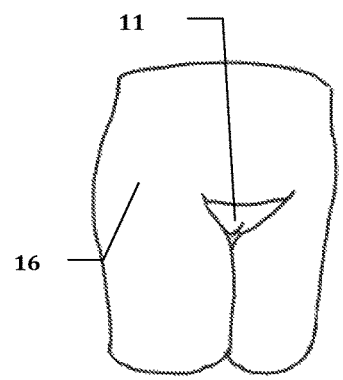
FIG. 6c: Perspective view of the female user in standing position after deployment of female condom.

FIG. 6a-c shows the preferred embodiment without the releasing sheet being attached. As aforementioned, it comprises two thin flexible membranous films sealed 18 in omega or similar shape with the seam at the base of the omega shape 2 comprising extended shield portion 11. The elongated omega shape portion would become the tubular portion 12 of the female condom. By deploying the female condom onto the female user 16 described above, the open end 13 would be ready for coitus (FIG. 6b). While the external genitalia are completely covered by the female condom, the anus may or may not be covered by the shield, all depending on the preferences of the user. It would then be just a matter of extending the posterior shield portion 23 during construction of the female condom if anus is to be covered.

FIG. 6c shows the female user 16 in standing position. As illustrated, the female condom is more secured, comfortable and aesthetically pleasing compared to Hessel's female condom discussed above, where the outer ring would be dangling outside the introitus in standing position.

Figure 7A:
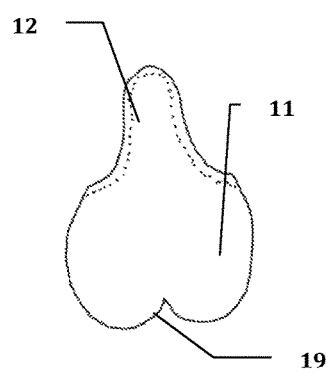
FIG. 7a-c: Drawings depicting the alternative shape of the shield portion with respect to FIG. 6a-c.
Figure 7B:
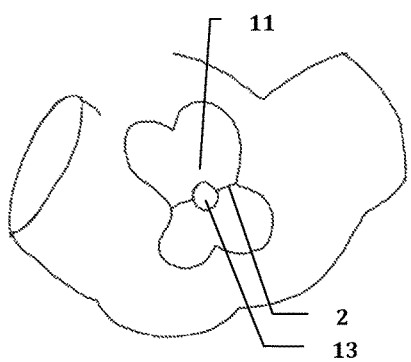
Figure 7C:
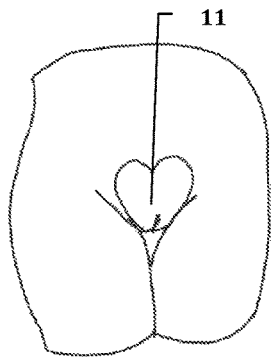

FIG. 7a-c shows an embodiment with a different shape for the shield portion. Instead of a rectangular shape, it has cut edges 19 resembling an inverted heart shape. On deployment it resembles a heart sitting at the pubic region.

Figure 8A:
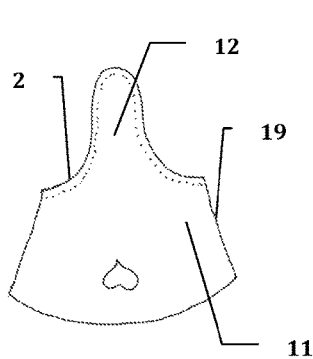
FIG. 8a-b: More drawings as in FIG. 7a-c.
Figure 8B:
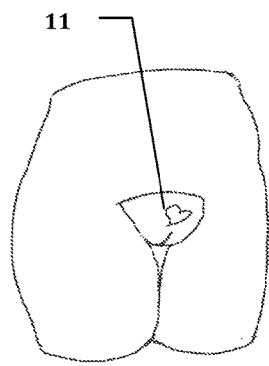
Figure 9:
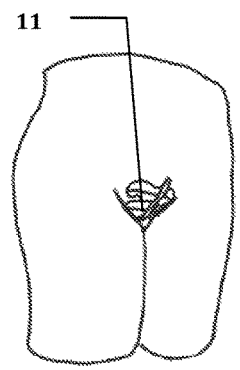
FIG. 9: A fig leaf design for the shield portion as in FIG. 6c.
Figure 10:
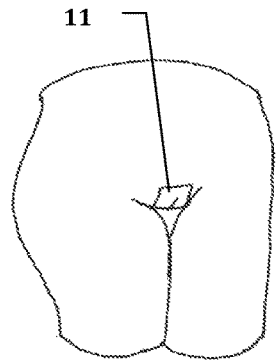
FIG. 10: As in FIG. 6c, a minimalist design for the shield portion covering the introitus only.

FIG. 8a shows another embodiment where the cut edges 19 is at an angle to the base of the omega shape 2. It gives the pubic region greater coverage 11 (FIG. 8b). FIG. 9 shows another embodiment with fig leaf shape shield portion 11, whereas FIG. 10 reveals a minimalist embodiment with hardly any pubic region being covered by the shield 11.

Figure 11A:
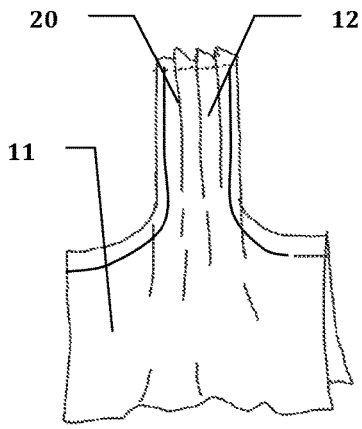
FIG. 11a: Perspective view of the female condom where the tubular portion is folded longitudinally.
Figure 11B:
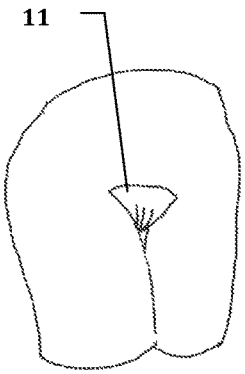

FIG. 11 shows another embodiment with longitudinal folds 20 at the tubular portion 12 of the female condom. The folds increase the capacity of the tubular portion at a given width, thereby putting less strain at the open end of the tubular portion during coitus.

Figure 12A:
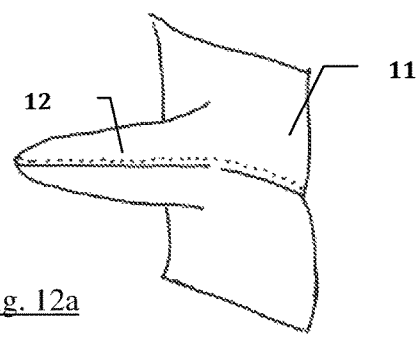
FIG. 12a: Perspective view of the female condom without the releasing paper/sheets attached.
Figure 12B:
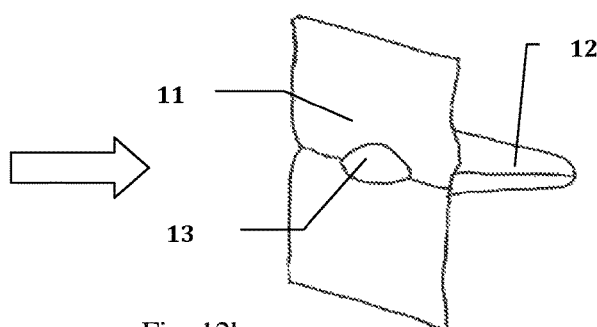
FIG. 12b: Perspective view of the female condom as FIG. 12a with the tubular portion being inverted, turning it into a male condom.
Figure 12D:
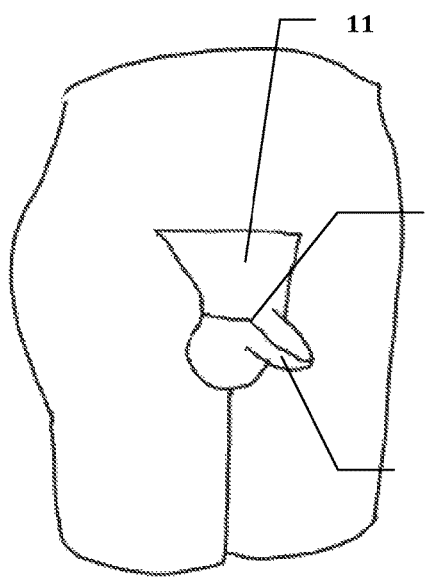
FIG. 12c-d: perspective view of the deployment of the male condom as in FIG. 12b onto a male user.
Figure 12C:
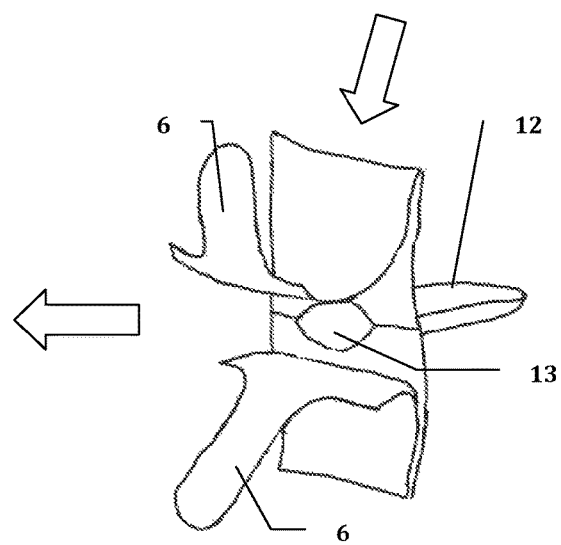

FIG. 12a-d describes how the present invention can be converted into a male condom by simply inverting the tubular end 12 inside out. The releasing sheets are not shown in FIG. 12a and b. In FIG. 12c, the releasing sheets are partially peeled while the open end 13 is donned onto the penis with the help of lubricant. The shield portion 11 is adhered to the pubic and scrotal region as shown. In this way man can equally be in control and be protected by the present invention.

As discussed above, the posterior shield portion 23 could be made to leave out the anus by just having a shorter shield 23 than the anterior shield 22 as shown in FIG. 13a-b. The dimension of the anterior and posterior part of the shield can be constructed according to the users' preferences.

In another embodiment the sealing of the two membranous films layers is done longitudinally, in this case the shield would be opened up sideway (FIG. 14a-b) with the seam at the base of the omega shape 2 running longitudinally. This embodiment allows the addition of an extra omega shape tubular region 24 for insertion into the anus 25 to enable safe anal sex (FIG. 15a-b). In case of male user, both the penis and anus can be protected in the same way (FIG. 15c).

Figure 16A:
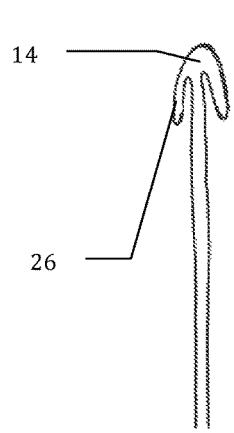
FIG. 16a: side view of the tubular portion with folded ends of FIG. 16b.
Figure 16B:
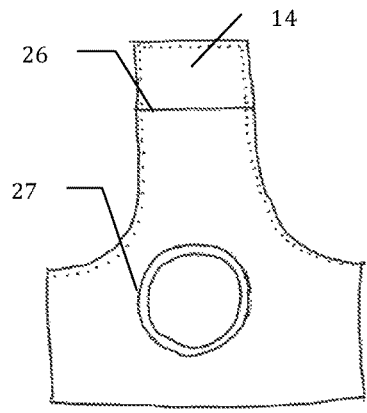
FIG. 16b: Front view of the female condom with the folded closed end, with vaginal ring pessary in the shield portion of the female condom.
Figure 16C:
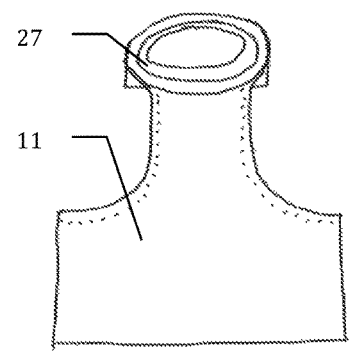
FIG. 16c: Perspective view of FIG. 16b with the ring pessary placed perpendicularly to the tubular portion.

FIG. 16 shows another embodiment specifically invented for the placement of a ring pessary 27 for anchoring the closed end of the tubular portion to the vagina. Both layers of membranous films at the rectangular closed end 14 is folded (for example, 5 to 25 mm) transversely 26 unto itself (FIG. 16a) before they are sealed as shown in FIG. 16b. The ring should have a diameter that is slightly smaller that the width of the tubular portion when it is lied flat. Because of the folding 26, the space at the closed end 14 is increased, thus allowing perpendicular placement of the ring pessary with in the closed end. This eliminates the problem of the ring pessary not staying at the closed end of the tubular portion during deployment of the female condom and during coitus.

Figure 17:
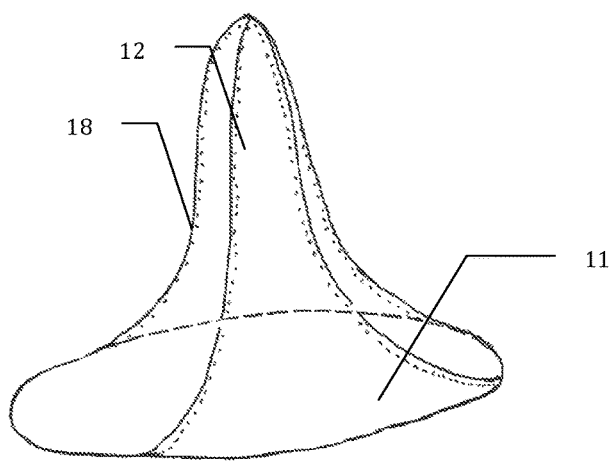
FIG. 17: Perspective view of the female condom made up of multiple pieces of thin membranous films sealed together, each thin membranous film forming part of both the tubular and the shield portions.

In another embodiment, the female condom can be made up of multiple membranous film sealed together to provide both the tubular and shield portions (FIG. 17) It has the advantage of putting less strain on the open end of the tubular portion during coitus, though the production process could be more complicated.

The present invention, at proper application, should completely seal off both the internal and the external genitalia of the female partner to prevent the exchange of genital fluid of both partners during coitus. And since it completely seals off the genitalia, it could conceal off unpleasant vaginal discharge, bleeding or odour. Also because of this, it has the potential for being use in different occasions such as in the bath, shower, swimming pool, sea, beach, and situations such as oral and anal sex without worrying about soiling and contamination. Depending on the opacity of the shield being constructed, it can also be used to cover up unsightly pubic hair, scars, anatomical deformity and pigmentations. It is also convenient to use, as it can be donned any time before sexual contact and removed any time after that. Furthermore, unlike regular condom, it can be used regardless of the varying degree of rigidity of the penis during sexual contact.

Due to the present invention's unique design, manufacturing process and the ease of donning, the thinnest possible membranous films could be employed to construct it. It is therefore able to provide better tactile and thermal sensitivity that the prior art.

My claims are:
1. A female condom comprising
   a. two layers of flexible, thin wall membranous films sealed together to form a seam having an omega shape, the condom comprising a shield portion and a tubular portion,
      wherein the seam that forms the base of the omega shape has two elongated flanges which form the shield portion of the female condom, while the tubular portion comprises a closed end and an open end with the closed end being formed by the seam,
      wherein the diameter of the open end is sufficiently large to permit insertion and movement of a penis, while the length of the tubular portion is sufficiently long enough to accommodate the entire penis,
      wherein the shield portion is sufficiently large to completely seal the external genitalia to prevent seepage of fluid from female genitalia,
   b. an adhesive on a first external surface of the shield, and
   c. one or more releasing paper/sheets on a second external surface of the shield which are removable from the second external surface of the shield.

2. The condom of claim 1, wherein the tubular portion includes a substantially elongated shape.

3. The condom of claim 1, wherein the shield portion is sufficiently large enough to cover enough external genitalia to prevent direct dermal contacts between the external genitalia of a user and her partner.

4. The condom of claim 1, wherein the adhesive is a hydrogel.

5. The condom of claim 1, wherein the adhesive is an ointment base.

6. The condom of claim 1, wherein the adhesive is medicated or enriched with health supplements and minerals.

7. The condom of claim 1, wherein the adhesive is applied partially or wholly onto the shield portion of the membranous film.

8. The condom of claim 1, wherein the tubular portion includes an internal and external portion; and
   the internal and/or external portion are pre-treated with ridges, studs and nubs.

9. The condom of claim 1, wherein the shield portion is designed to be in various shapes, sizes, colours, opacity, textures, added pictures, wordings and logos.

10. The condom of claim 1, wherein the condom is lubricated, perfumed and/or flavoured.

11. The condom of claim 1, wherein the sizes of the tubular and shield portions for the external genitalia and the lower part of the body are made according to different body build and the preferred area of coverage of the users.

12. The condom of claim 1, wherein the size and shape of the anterior and posterior parts of the shield are constructed to suit users' preferences.

13. The condom of claim 1, wherein the tubular portion is inverted to turn it into a male condom.

14. A method of making the condom of claim 1, wherein the omega shape seal of the membranous films is made such that the seam is perpendicular to the direction the releasing paper/sheets are removed from the shield.

15. The condom of claim 1 further comprising a second tubular portion to allow both vaginal and anal intercourses for both female and male users.

16. The condom of claim 1, wherein the tubular portion further comprises one or more longitudinal folds.

17. The condom of claim 1, wherein both layers of membranous films at the closed end of the tubular portion comprise one or more transverse folds.

18. A method of making the condom of claim 1 comprising a step of sealing of more than two pieces of membranous films, each making up a part of both the tubular and shield portions.

19. A method of making the condom of claim 1 comprising the steps:
   a) Sealing a first layer of membranous film to a second layer of membranous film,
   b) applying adhesive to a first side of the membranous films.
   c) applying releasing paper or a plastic sheet to a second side of the on the other membranous film, and
   d) Cutting the membranous films into final product.

\* \* \* \* \*